United States Patent [19]

Black

[11] 4,058,663

[45] Nov. 15, 1977

[54] STABILIZATION WITH ALKALI METAL COMPOUND MATERIAL OF CERTAIN THERMALLY UNSTABLE DMT

[75] Inventor: Donald Kirkbright Black, New Castle County, Del.

[73] Assignee: Hercules Incorporated, Wilmington, Del.

[21] Appl. No.: 663,165

[22] Filed: Mar. 2, 1976

[51] Int. Cl.$^2$ ............................................. C07C 69/82
[52] U.S. Cl. ....................................................... 560/3
[58] Field of Search ..................................... 260/475 B

[56] References Cited

U.S. PATENT DOCUMENTS

| | | | |
|---|---|---|---|
| 3,461,153 | 8/1969 | Tholstrup et al. | 260/475 B |
| 3,642,871 | 2/1972 | Tholstrup et al. | 260/475 B |

Primary Examiner—Jane S. Myers
Attorney, Agent, or Firm—George H. Hopkins

[57] ABSTRACT

Disclosed is the stabilization of thermally unstable, fresh dimethyl terephthalate of at least 99.8 weight % purity, free of alkali metal compound material, and produced by the cooxidation-esterification process. Stabilization is effected by incorporating therein a stabilizing quantity of alkali metal compound material having no significant concentration of either phosphonic acid moiety or phosphite moiety.

8 Claims, No Drawings

STABILIZATION WITH ALKALI METAL COMPOUND MATERIAL OF CERTAIN THERMALLY UNSTABLE DMT

This invention is in the chemical arts. It has to do with that branch of organic chemistry pertaining to alcohol esters of aromatic dicarboxylic acids.

In particular, it relates to dimethyl terephthalate (DMT), and particularly to the thermal stabilization of thermally unstable DMT.

DMT is a basic chemical for the production of polyethylene terephthalate polymers from which fibers and the like are made. It is producd in large tonnages in extremely high purity, that is, a purity of at least 99.8% by weight and typically in the case of one producer of a purity of 99.99% by weight. A common practice is to ship, store and use DMT in the molten state, that is, at temperatures above 140° C. DMT of extremely high purity, however, is not thermally stable in that there is a tendency for the color and acid number of it to increase rapidly to unacceptable values when it is maintained in the molten state. Consequently, the thermal stabilization of thermally unstable DMT has received a fair amount of attention in the art.

One approach to the problem has been to incorporate additives into the thermally unstable DMT. Representative of this approach and of the additives are the following: the U.S. Pat. No. 3,445,504, to Mehalso (a hindered phenol plus a dialkyl phosphite), the U.S. Pat. No. 3,461,153, to Tholstrup et al. (alkali metal salts or alkoxides, plus certain phosphites), the U.S. Pat. No. 3,485,867, to Jackson (ethylene glycol), the U.S. Pat. No. 3,505,390, to Hoffmann (methanol), the U.S. Pat. No. 3,659,007, to Giambra (catechol and pyrogallol), the U.S. Pat. No. 3,742,025, to Mori et al. (P-aryl and P-aralkyl substituted phosphonic acids, and esters and alkali metal salts thereof), the U.S. Pat. No. 3,742,026, to Mori et al. [bis($\beta$-hydroxyethyl)terephthalate], and the U.S. Pat. No. 3,742,027, to Mori et al. ($C_1$-$C_7$ alkanol material plus cobalt salt material).

For one reason or another, the additives or mixtures of additives taught by the foregoing patents as being effective have one or more disadvantages. This invention avoids these disadvantages.

In particular, this invention provides ways and means for thermally stabilizing thermally unstable fresh DMT of extremely high purity, free of alkali metal compound material, and produced by the cooxidation-esterification process. This process as practised commercially is a continuous process. It comprises effecting in an oxidation zone with a catalytic quantity of halide-free catalyst material consisting essentially of cobalt or a halide-free salt thereof, manganese or a halide-free salt thereof, or cobalt and maganese or halide-free salts thereof the cooxidation with molecular oxygen of p-xylene in the liquid phase and methyl p-toluate without adding to the oxidation zone halogen or halide containing material, a solvent such as, for example, acetic acid, or initiators such as, for example, acetaldehyde, methyl ethyl ketone, and the like. The resulting reaction mixture comprises p-toluic acid and monoethyl terephthalate. Reaction mixture is withdrawn from the oxidation zone and at least part of it, which part comprises p-toluic acid, monomethyl terephthalate and the catalyst material, is introduced into an esterification zone wherein reaction with methanol is effected to form an esterification reaction mixture comprising methyl p-toluate and DMT. Esterification reaction mixture is withdrawn from the esterification zone and separated into a methyl p-toluate fraction which is introduced into the oxidation zone, and a DMT fraction which is treated to isolate DMT in extremely high purity.

In view of what follows it is important to bear in mind that the cooxidation-esterification process is different from other DMT production processes, and that DMT of extremely high purity produced by the cooxidation-esterification process differs from DMT of extremely high purity produced by other processes in that apparently there are significant differences in impurities and concentrations thereof therein. All of the impurities and their concentrations are not known with certainty.

In summary, this invention comprises a thermally stable composition consisting essentially of (1) thermally unstable, fresh DMT of extremely high purity, free of alkali metal material and produced by the cooxidation-esterification process, and (2) dispersed therein at a stabilizing concentration, alkali metal compound material having no significant concentration of either phosphonic acid moiety or phosphite moiety.

Fresh DMT of extremely high purity is DMT of extremely high purity in which thermal degradation has not progressed to the point the ASTM Pt-Co color value thereof has changed significantly from the ASTM Pt-Co color value thereof when isolated in the process of producing it. In this connection there is evidence that when thermal degradation of DMT of extremely high purity, free of alkali compound material and produced by the cooxidation-esterification process has progressed to the point of a significant change in the ASTM Pt-Co color value thereof, the thermal stabilizing effect of the alkali metal compound material of this invention is drastically diminished.

Alkali metal compound material having no significant cencentration of either phosphonic acid moiety or phosphite moiety is material selected from the group consisting of alkali metal oxides, hydroxides, alkoxides and salts having no phosphonic acid moiety and no phosphite moiety. Phosphonic acid moiety as used herein refers to

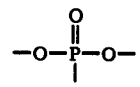

while phosphite moiety as used herein refers to

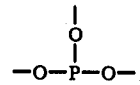

Alkali metal as used herein includes lithium, sodium, potassium, rubidium and cesium. Preferred, however, because of availability and cost, are the sodium and potassium compounds. Examples of sodium compounds of this invention are sodium oxide, sodium hydroxide, sodium carbonate, sodium methoxide, sodium ethoxide, sodium formate, sodium acetate, sodium propionate, sodium citrate, sodium sorbate, sodium benzoate, sodium p-toluate, sodium monomethyl terephthalate, sodium naphthoate, and the like. Examples of potassium compounds of this invention are potassium oxide, potassium hydroxide, potassium methoxide, potassium ethoxide, and the potassium salts of carbonic acid, acetic acid, propionic acid, citric acid, sorbic acid, p-toluic acid, monoethyl terephthalate, naphthoic acid, and the like. In some embodiments of the invention the alkali metal compound material comprises only one compound. In other embodiments of the invention it comprises two or more alkali metal compounds, but in neither case is there a significant concentration of either phosphonic acid moiety or phosphite moiety.

Concentration of the alkali metal compound material in the thermally stable composition of this invention is in a wide range. Generally, however, it is in a range from about 0.5 to about 500 parts by weight per million parts by weight of the thermally unstable DMT with 1-20 parts by weight per million parts by weight of the thermally unstable DMT being recommended in most embodiments of the composition of this invention.

The composition of this invention is made in several ways.

In one procedure it is made by admixing the alkali metal compound material with the thermally unstable DMT in the molten state. This admixing can be done by adding the alkali metal compound material to the molten DMT while stirring it. Preferably, the more basic it is, the slower it is added so as to minimize saponification of DMT. It also can be done by blowing with an inert gas the alkali metal compound material into the molten DMT. In either case the resulting molten composition can be maintained in the molten state until it is used, or it can be cooled until solid.

In another procedure the composition of this invention is made by admixing the alkali metal compound material with the thermally unstable DMT in the finely divided solid state. At the time the alkali metal compound material can be in the finely divided solid state, the molten state or dissolved in an inert solvent which subsequently, if desired, is removed by evaporation. Thereafter, when the DMT is melted for use, the stabilizing material automatically is incorporated in it.

In still another procedure the composition of this invention is made by admixing the alkali metal compound material with a solution of the thermally unstable DMT in a solvent preferably for both the DMT and the alkali metal compound material. Preferably, the alkali metal compound material when added to the solution is dissolved either in a mutual solvent or the same solvent. After the alkali metal compound has been dispersed in the solvent of DMT, the solvent is removed by evaporation, or crystallization of the DMT is effected. In either case the solid DMT has incorporated in it the alkali metal compound material of this invention.

In yet another procedure the alkali metal compound material is admixed with molten DMT so that the concentration of the alkali metal compound material is substantially higher then the ultimate use concentration. The concentrate thus formed can be maintained in the molten state, or it can be cooled until solid. In either case a stabilizing quantity of the concentrate thus formed is subsequently added to the DMT to be stabilized.

The efficacy of the alkali metal compound material of this invention in stabilizing the thermally unstable DMT described above is demonstrated by the following tabulated data obtained on samples of specific embodiments of the composition of this invention. The data were obtained in a test procedure in which 40 gram samples of solid, unstabilized, fresh DMT of extremely high purity, free of alkali metal compound material and produced in a commercial plant based on the cooxidation-esterification process, ground to a particle size of minus 3 mesh (U.S. screen size), admixed, (except in the case of the control sample) with the additive to be tested, are heated in 8 inch by 1 inch Pyrex glass tubes covered with aluminum foil at 175 ± 2° C. for 24 hours. In those tests in which the concentration of the additive is greater than 10 parts per million of unstabilized DMT, the additive is weighed directly and then admixed with the unstabilized DMT. In those tests involving additive concentrations less than 10 parts per million of unstabilized DMT, the additive is dissolved in methanol to give a solution of known concentration, and a predetermined volume of the solution is admixed with the DMT sample in the glass tube to give the desired concentration off additive. In such tests the same volume of methanol as used for the addition of additive to the samples is admixed with the control sample. At the end of the 24 hours heating period the ASTM Pt-Co color is measured and the acid number determined for each sample.

Test Series I

| Additive: Potassium Monomethyl Trephthalate | | | |
|---|---|---|---|
| Sample No. | Additive Conc. (p.p.m.) | Pt-Co Color | Acid No. |
| Control | 0 | 110 | 0.74 |
| 1 | 10 | 5 | 0.02 |
| 2 | 10 | 10 | 0.03 |
| 3 | 50 | 5 | 0.04 |
| 4 | 100 | 5 | 0.04 |
| 5 | 250 | 5 | 0.03 |
| 6 | 500 | 5 | 0.04 |

Test Series II

| Additive: Sodium Benzoate | | | |
|---|---|---|---|
| Sample No. | Additive Conc. (p.p.m.) | Pt-Co Color | Acid No. |
| Control | 0 | 120 | 0.85 |
| 1 | 10 | 5 | 0.05 |
| 2 | 10 | 5 | 0.05 |

Test Series III

| Additive: Sodium Benzoate | | | |
|---|---|---|---|
| Sample No. | Additive Conc. (p.p.m.) | Pt-Co Color | Acid No. |
| Control | 0 | 120 | 0.80 |
| 1 | 10 | 10 | 0.04 |
| 2 | 10 | 10 | 0.04 |

Test Series IV

| Additive: Potassium Acid Phthalate | | | |
|---|---|---|---|
| Sample No. | Additive Conc. (p.p.m.) | Pt-Co Color | Acid No. |
| Control | 0 | 100 | 0.78 |
| 1 | 10 | 15 | 0.09 |
| 2 | 10 | 20 | 0.09 |

Test Series V

| Additive: Potassium Acid Phthalate | | | |
|---|---|---|---|
| Sample No. | Additive Conc. (p.p.m) | Pt-Co Color | Acid No. |
| Control | 0 | 130 | 0.72 |
| 1 | 5 | 30 | 0.02 |
| 2 | 5 | 40 | 0.06 |

Test Series VI

Additive: Potassium Acid Phthalate

| Sample No. | Additive Conc. (p.p.m.) | Pt-Co Color | Acid No. |
|---|---|---|---|
| Control | 0 | 120 | 0.87 |
| 1 | 10 | 20 | 0.07 |
| 2 | 10 | 20 | 0.07 |

Test Series VII

Additive: Sodium Hydroxide

| Sample No. | Additive Conc. (p.p.m.) | Pt-Co Color | Acid No. |
|---|---|---|---|
| Control | 0 | 110 | 0.85 |
| 1 | 1 | 10 | 0.01 |
| 2 | 1 | 10 | 0.02 |

Test Series VIII

Additive: Sodium Hydroxide

| Sample No. | Additive Conc. (p.p.m.) | Pt-Co Color | Acid No. |
|---|---|---|---|
| Control | 0 | 100 | 0.84 |
| 1 | 1 | 10 | 0.03 |
| 2 | 1 | 15 | 0.09 |

Test Series IX

Additive: Sodium Hydroxide

| Sample No. | Additive Conc. (p.p.m.) | Pt-Co Color | Acid No. |
|---|---|---|---|
| Control | 0 | 110 | 0.91 |
| 1 | 2 | 15 | 0.05 |
| 2 | 2 | 15 | 0.07 |

Test Series X

Additive: Sodium Hydroxide

| Sample No. | Additive Conc. (p.p.m.) | Pt-Co Color | Acid No. |
|---|---|---|---|
| Control | 0 | 120 | 0.79 |
| 1 | 1 | 20 | 0.07 |
| 2 | 1 | 30 | 0.06 |

Test Series XI

Additive: Sodium Hydroxide

| Sample No. | Additive Conc. (p.p.m.) | Pt-Co Color | Acid No. |
|---|---|---|---|
| Control | 0 | 120 | 0.77 |
| 1 | 1 | 70 | 0.54 |
| 2 | 1 | 70 | 0.56 |
| 3 | 2 | 20 | 0.05 |
| 4 | 2 | 25 | 0.06 |
| 5 | 4 | 15 | 0.04 |
| 6 | 4 | 15 | 0.05 |

Test Series XII

Additive: Potassium Hydroxide

| Sample No. | Additive Conc. (p.p.m.) | Pt-Co Color | Acid No. |
|---|---|---|---|
| Control | 0 | 100 | 0.90 |
| 1 | 2 | 10 | 0.02 |
| 2 | 4 | 10 | 0.03 |

Test Series XIII

Additive: Potassium Hydroxide

| Sample No. | Additive Conc. (p.p.m.) | Pt-Co Color | Acid No. |
|---|---|---|---|
| Control | 0 | 120 | 0.87 |
| 1 | 2 | 10 | 0.02 |
| 2 | 4 | 10 | 0.03 |

The following data were obtained as above except that the samples were maintained at 175 ± 2° C. for 3 days and then the Pt-Co Color and Acid No. values obtained.

Test Series XIV

Additive: Potassium Acetate

| Sample No. | Additive Conc. (p.p.m.) | Pt-Co Color | Acid No. |
|---|---|---|---|
| Control | 0 | >150 | 0.62 |
| 1 | 2 | 10 | 0.07 |
| 2 | 2 | 10 | 0.05 |
| 3 | 5 | 10 | 0.28 |
| 4 | 5 | 10 | 0.35 |
| 5 | 10 | 10 | 0.39 |
| 6 | 10 | 15 | 0.31 |

These data demonstrate that alkali metal compounds free of either phosphonic acid moiety or phosphite moiety are effective stabilizers for thermally unstable DMT produced by the oxidation esterification process.

Use of phenolics, e.g., catechol, to stablize molten DMT can lead to the introduction of impurities into the DMT by oxidation to colored 1,2-benzoquinones at the temperatures used (>150° C.). In addition, catechol has a tendency to sublime at storage temperatures leading to loss of stabilization. The alkali metal compounds of this invention, particularly potassium monomethyl terephthalate, sodium hydroxide and potassium hydroxide, do not have these undesirable features.

The alkali metal compounds of this invention are far superior to bis($\beta$-hydroxyethyl) terephthalate which in the U.S. Pat. No. 3,742,026 is disclosed to stabilize DMT at concentrations ranging from 0.03 to 3% by weight. They are also superior to the phosphonic acid derivatives described by Mori et al. in the U.S. Pat. No. 3,742,025 in that in general, higher concentrations of these derivatives are required to give the equivalent 24 hour color values obtained with 1-2 p.p.m. of alkali metal compound material of this invention. No acid number values are available from the patent for comparison.

A surprising aspect of this invention is the effectiveness of the alkali metal compounds of this invention at the recommended concentrations thereof in thermally unstable DMT. The U.S. Pat. No. 3,461,153, to Tholstrup et al, cited at the beginning of this specification, contains data from which it can be concluded that alkali metal compounds alone at 20 parts per million parts of DMT do not stabilize thermally unstable DMT against color change at temperatures in excess of 140° C. The only explanations for the apparent inconsistency between the data of the Tholstrup et al. patent and the data reported in this specification are that the DMT involved in the testing reported in the Tholstrup et al. patent was produced by a process other than the cooxidation-esterification process, that the DMT in the Tholstrup et al. patent was not fresh, or both.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

The expression "consisting essentially of" as used in this specification excludes any unrecited substance at a concentration sufficient to substantially adversely affect the essential properties and characteristics of the composition of matter being defined, while permitting the presence of one or more unrecited substances at concentrations insufficient to substantially adversely affect said essential properties and characteristics.

I claim:

1. A thermally stable composition consisting essentially of (1) thermally unstable fresh dimethyl terephthalate of extremely high purity, free of alkali metal compound material, having no significant concentration of either phosphonic acid moiety or phosphite moity, and produced by the cooxidationesterification process, and (2) dispersed therein at a stabilizing concentration, alkali metal monomethyl terehthalate.

2. A thermally stable composition according to claim 1 in which the concentration of said alkali metal monomethyl terephthalate is in the range from about 0.5 to about 500 parts by weight per million parts by weight of said DMT.

3. A thermally stable composition according to claim 2 in which the concentration of said alkali metal monomethyl terephthalate is 1-20 parts by weight per million parts by weight of said DMT.

4. A thermally stable composition according to claim 3 in which said alkali metal monomethyl terephthalate is potassium monomethyl terephthalate.

5. A process for stabilizing thermally unstable fresh dimethyl terephthalate of extremely high purity, free of alkali metal compound material, having no significant concentration of either phosphonic acid moiety or phosphite moiety, and produced by the cooxidation-esterification process, which comprises incorporating into said dimethyl terephthalate a stabilizing quantity of alkali metal monomethyl terephthalate.

6. A process according to claim 5 in which said quantity is about 0.5 to about 500 parts by weight per million parts by weight of said DMT.

7. A process according to claim 6 in which the quantity of said alkali metal monomethyl terephthalate is 1-20 parts by weight per million parts by weight of said DMT.

8. A process according to claim 7 in which said alkali metal monomethyl terephthalate is potassium monomethyl terephthalate.

* * * * *